(12) United States Patent
Venkataramani et al.

(10) Patent No.: US 10,368,846 B2
(45) Date of Patent: Aug. 6, 2019

(54) CLASSIFYING HORMONE RECEPTOR STATUS OF MALIGNANT TUMOROUS TISSUE FROM BREAST THERMOGRAPHIC IMAGES

(71) Applicant: Niramai Health Analytix Pvt. Ltd., Bangalore (IN)

(72) Inventors: Krithika Venkataramani, Bangalore (IN); Siva Teja Kakileti, Kakinada (IN); Himanshu J. Madhu, Mumbai (IN)

( * ) Notice: Subject to any disclaimer, the term of this patent is extended or adjusted under 35 U.S.C. 154(b) by 50 days.

(21) Appl. No.: 15/636,739

(22) Filed: Jun. 29, 2017

(65) Prior Publication Data

US 2018/0000462 A1   Jan. 4, 2018

Related U.S. Application Data

(60) Provisional application No. 62/356,208, filed on Jun. 29, 2016.

(51) Int. Cl.
*G06K 9/00* (2006.01)
*A61B 10/00* (2006.01)
(Continued)

(52) U.S. Cl.
CPC .......... *A61B 10/0041* (2013.01); *A61B 5/015* (2013.01); *A61B 5/4312* (2013.01);
(Continued)

(58) Field of Classification Search
None
See application file for complete search history.

(56) References Cited

U.S. PATENT DOCUMENTS

| 4,428,382 A * | 1/1984 | Walsall | A61B 5/015 600/549 |
| 10,206,632 B2 * | 2/2019 | Halter | A61B 5/7246 |

(Continued)

OTHER PUBLICATIONS

Zore et al ("Influence of Hormonal Status on Thermography Findings in Breast Cancer", Department of Surgical Oncology, Sestre milosrdnice University Hospital Center, Ilica 197, HR-10000 Zagreb, Croatia, Received May 24, 2012, accepted Dec. 16, 2012).*

(Continued)

*Primary Examiner* — Shervin K Nakhjavan
(74) *Attorney, Agent, or Firm* — The Law Office of Austin Bonderer, PC; Austin Bonderer

(57) ABSTRACT

What is disclosed is a system and method for classifying the hormone receptor status of malignant tumorous tissue identified in a thermographic image of a breast. One embodiment of the present method involves the following. First, receive thermographic image(s) of both breasts of a patient with a malignant tumorous region and analyzing the image(s) to define a boundary contour of the breast. Then, the breast regions are segment into regions of elevated temperature. A function of first probability mass function Q, $f(Q)$, is determined based on temperatures of pixels within a first segmented region. A function of the second probability mass function P, $f(P)$, is determined based on temperatures of pixels within a second region. A distance measure between the two functions $f(Q)$ and $f(P)$ is calculated and provided to a classifier trained to classify the malignant tissue as hormone receptor positive, and negative otherwise, based on the distance measure.

27 Claims, 9 Drawing Sheets

(51) Int. Cl.
*A61B 5/01* (2006.01)
*C07K 16/28* (2006.01)
*C12Q 1/6886* (2018.01)
*A61B 5/00* (2006.01)
*G06T 7/00* (2017.01)
*G06T 7/11* (2017.01)
*G01N 33/574* (2006.01)

(52) U.S. Cl.
CPC .......... *A61B 5/489* (2013.01); *C07K 16/2869* (2013.01); *C12Q 1/6886* (2013.01); *G06T 7/0012* (2013.01); *G06T 7/11* (2017.01); *A61B 5/00* (2013.01); *A61B 2576/02* (2013.01); *G01N 33/57415* (2013.01); *G06T 2207/10048* (2013.01); *G06T 2207/30068* (2013.01)

(56) References Cited

U.S. PATENT DOCUMENTS

| | | | | |
|---|---|---|---|---|
| 2002/0193849 A1* | 12/2002 | Fenn | ......... | A61N 5/02 607/89 |
| 2005/0053958 A1* | 3/2005 | Roth | ......... | C12Q 1/6886 435/6.16 |
| 2008/0166301 A1* | 7/2008 | Hanson | ......... | A61K 31/56 424/9.4 |
| 2009/0047215 A1* | 2/2009 | Harris | ......... | C12Q 1/6886 424/1.89 |
| 2010/0312136 A1* | 12/2010 | Cozzie | ......... | A61B 5/015 600/549 |
| 2015/0254840 A1* | 9/2015 | Madabhushi | ......... | G06T 7/0012 382/131 |
| 2016/0206211 A1* | 7/2016 | Naimi | ......... | A61B 5/0091 |

OTHER PUBLICATIONS

Kuruganti et al ("Asymmetry Analysis in Breast Cancer Detection Using Thermal Infrared Images", Proceedings 01 the Second Joint EMBSiBMES Conference Houston, TX USA *Oct. 23-26, 2002).*

Borchartt et al ("Breast thermography from an image processing viewpoint: A survey", Signal Processing 93, 2785-2803, 2013).*

Ohsumi et al ("Prognostic value of thermographical findings in patients with primary breast cancer", Breast Cancer Research and Treatment 74: 213-220, 2002).*

* cited by examiner

| FEATURE SET | FEATURES | HR- ACCURACY | HR+ ACCURACY |
|---|---|---|---|
| ABNORMAL REGION FEATURES | DISTANCE BETWEEN REGIONS | 74% | 55% |
| | RELATIVE HOTNESS | 90% | 55% |
| | THERMAL DISTRIBUTION RATIO | 63% | 27% |
| | COMBINATION OF ABOVE THREE FEATURES | 84% | 73% |
| ENTIRE ROI FEATURES | GRAY-LEVEL NON-UNIFORMITY | 68% | 64% |
| OVERALL FEATURES | COMBINATION OF FEATURES FROM ABNORMAL AND ENTIRE ROI REGIONS | 79% | 82% |

FIG. 9
(TABLE 1)

US 10,368,846 B2

CLASSIFYING HORMONE RECEPTOR STATUS OF MALIGNANT TUMOROUS TISSUE FROM BREAST THERMOGRAPHIC IMAGES

TECHNICAL FIELD

The present invention is directed to systems and methods for classifying the hormone receptor status of malignant tumorous tissue identified in a thermographic image of a breast based on a distance measure.

BACKGROUND

Breast cancer is one of the highest incidences among cancers in women. Breast cancer also has wide variations in the clinical and pathological features, which are taken into account for treatment planning, and to predict survival rates or treatment outcomes. Thermography detects the temperature increase in malignancy due to the increased metabolism of cancer cells. The hormone receptor status of a malignant tumor is known to play a role in treatment planning and survival prediction. A hormone receptor is a protein found within and on a surface of certain cells throughout the body. When the right hormone attaches to a cell's receptor, like a key into a lock, a signal is communicated to the cell to turn ON/OFF a particular activity which that cell performs. One type of receptor found in breast cells is the hormone receptor. Knowledge of which hormone receptors are associated with a given hot spot seen within a thermographic image of a patient's breast can be useful for treatment planning and estimating mortality risk. The present invention is directed to this effort.

BRIEF SUMMARY

What is disclosed is a system and method for classifying the hormone receptor status of malignant tumorous tissue identified in a thermographic image of a breast. One embodiment of the present method involves the following. First, receive thermographic image(s) of both breasts of a patient with a malignant tumorous region and analyzing the image(s) to define a boundary contour of the breast in the image(s). Then, segment the breast regions into regions of elevated temperature and otherwise. Determine a function of first probability mass function Q, $f(Q)$, based on temperature values of pixels within a first segmented region. Determine a function of the second probability mass function P, $f(P)$, based on temperature values of pixels within a second segmented region. Determine a distance measure between the two functions $f(Q)$ and $f(P)$. Provide the distance measure to a classifier system trained to classify the malignant tumorous tissue as being hormone receptor positive, and hormone receptive negative otherwise.

In another embodiment disclosed herein, a thermographic image of a breast of a patient with tumorous tissue is received along with a thermographic image of the contra-lateral breast of that patient. The thermographic image of the contra-lateral breast is analyzed to identify a hot spot therein. The hot spot being defined as a patch of pixels with an elevated temperature with respect to a temperature of pixels in surrounding tissue. In response to a hot spot having been identified in the image of the contra-lateral breast, a distance measure is extracted. The distance measure comprises a sum of a mean squared difference between temperatures $T(x,y)$ at each $(x,y)$ pixel location in the tumorous tissue and a mean temperature $\mu$ of pixels comprising the hot spot identified in the contra-lateral breast. The distance measure is provided to a classifier system trained to classify tumorous tissue as being hormone receptor positive, and hormone receptive negative otherwise, based on the distance measure.

Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which:

FIG. 9 is a Table which shows accuracies obtained using individual features using the methods disclosed herein and discussed with respect to the flow diagram of FIG. 6 and the functional block diagram of FIG. 7.

DETAILED DESCRIPTION

What is disclosed is a system and method for classifying the hormone receptor status of malignant tumorous tissue identified in a thermographic image of a breast.

Non-Limiting Definitions

A "patient" refers to either a male or a female person. Gender pronouns are not to be viewed as limiting the scope of the appended claims strictly to females. Moreover, although the terms "subject", "person" or "patient" are used interchangeably throughout this disclosure, it should be appreciated that the patient undergoing cancer screening may be something other than a human such as, for example, a primate. Therefore, the use of such terms is not to be viewed as limiting the scope of the appended claims to humans.

Figure 1:
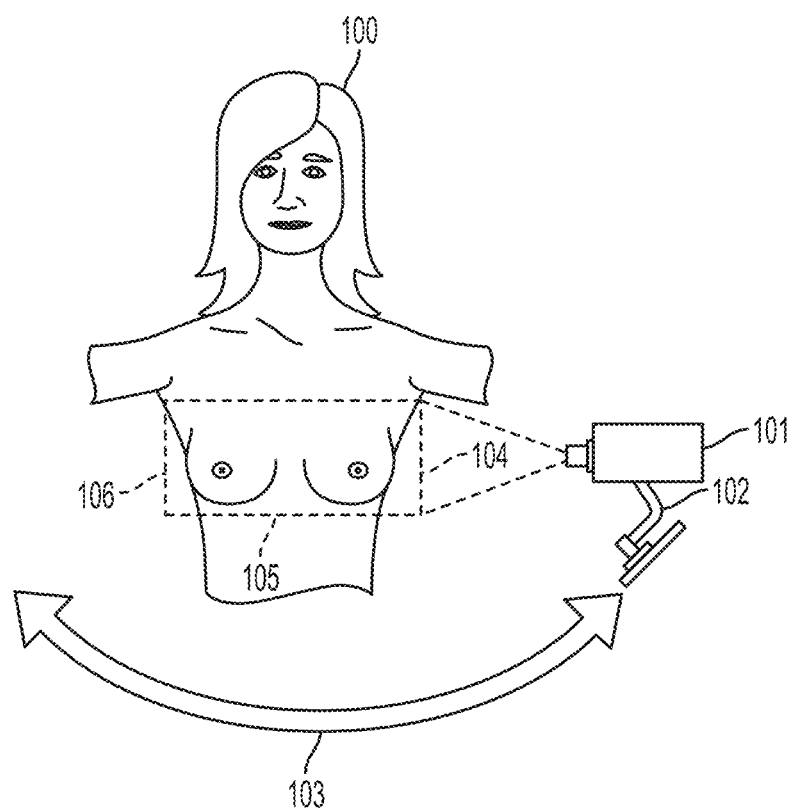
FIG. 1 shows an example female patient with a thermal camera mounted on a slideable and axially rotatable robotic arm for moving the camera along a semi-circular trajectory from side-to-side in front of the patient.

A "thermal camera" refers to either a still camera or a video camera with a lens that focuses infrared energy from objects in a scene onto an array of specialized sensors which convert infrared energy into electrical signals on a per-pixel basis and outputs a thermal image comprising an array of pixels with color values corresponding to temperatures of the objects in the image across a desired thermal wavelength band. FIG. 1 shows a thermal camera 101 mounted on a slideable and axially rotatable robotic arm 102 capable of moving the camera along a semi-circular trajectory 103 in the front of the patient from side-to-side such that thermographic images can be captured in a right-side view 104, a front view 105, and a left-side view 106, and various oblique angles in between. The thermal camera can be any of: a single-band infrared camera, a multi-band infrared camera in the thermal range, and a hyperspectral infrared camera in the thermal range. The resolution for a thermal camera is effectively the size of the pixel. Smaller pixels mean that more pixels will go into the thermal image giving the resulting image higher resolution and thus better spatial definition. Although thermal cameras offer a relatively large dynamic range of temperature settings, it is preferable that the camera's temperature range be relatively small, centered around the person's body surface temperature so that small temperature variations are amplified in terms of pixel color changes to provide a better measure of temperature variation. Thermal cameras are readily available in various streams of commerce. In one embodiment, the thermal camera is placed in wired or wireless communication with a workstation which enables manual or automatic control of various aspects of the thermal camera such as, for instance, adjusting a focus of the thermal camera lens, changing a resolution of the thermal camera, and changing a zoom level of the thermal camera.

Figure 2:
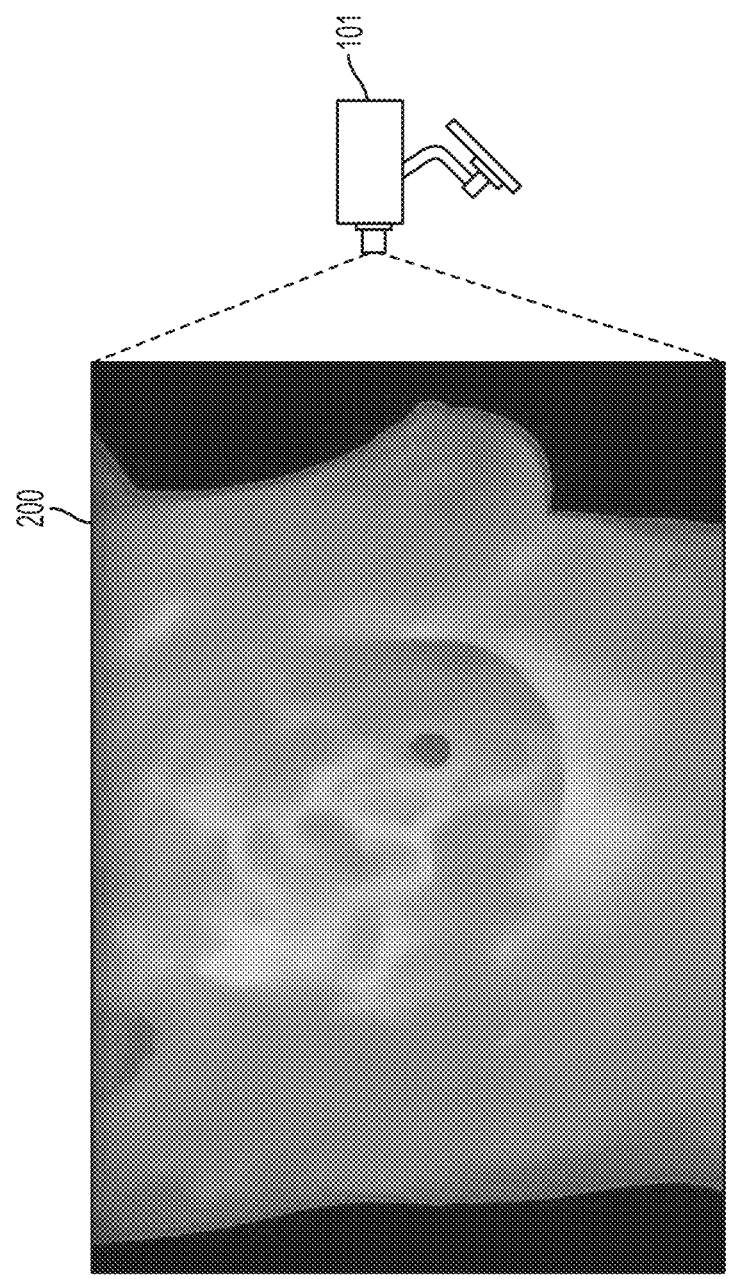
FIG. 2 shows a thermal image 200 of an oblique view of a breast area.
Figure 3:
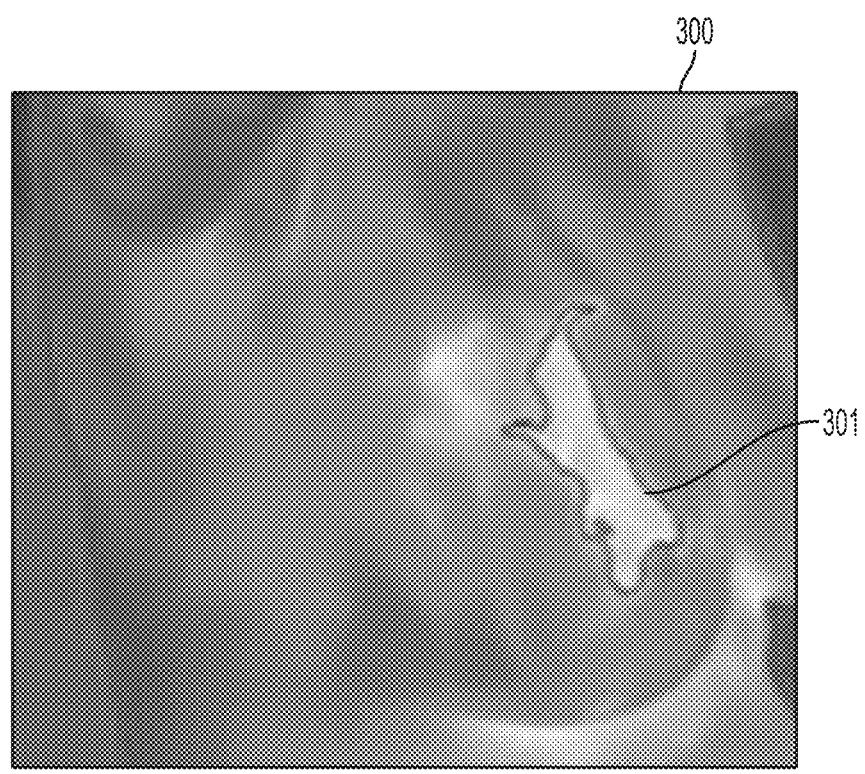
FIG. 3 shows a thermal image 300 of a left breast containing hot spot 301.

A "thermographic image" or simply "thermal image" comprises a plurality of pixels with each pixel having an associated corresponding temperature value. Pixels in the thermal image with a higher temperature value being displayed in a first color and pixels with a lower temperature value are displayed in a second color. Pixels with temperature values between the lower and higher temperature values are displayed in gradations of color between the first and second colors. FIG. 2 shows a thermal image 200 of an oblique view of a breast. Although shown in black/white, it should be appreciated that the thermal image is a color image. FIG. 3 shows a thermal image 300 of a breast wherein a hot spot 301 is identified. Thermal images can be retrieved from a memory or storage device of the thermal imaging device, or obtained from a remote device over a network. Thermal images may be retrieved from a media such as a CDROM or DVD. Thermal images may be downloaded from a web-based system which makes such images available for processing. Thermal images can also be retrieved using an application such as those which are widely available for handheld cellular devices and processed on the user's cellphone or other handheld computing device such as an iPad or tablet. Use of the term "image" is intended to also mean "video". This thermal image can also be stored and retrieved purely as a two-dimensional matrix of real numbered values (also known as radiometric image) which are derived as a function of the measured temperature values that are represented by the color of each pixel in the thermal image.

"Receiving a thermal image" of a patient for cancer screening is intended to be widely construed and includes retrieving, capturing, acquiring, or otherwise obtaining video image frames. The image can be received or retrieved from a remote device over a network, or from a media such as a CDROM or DVD. The image may be downloaded from a web-based system or application which makes video available for processing in accordance with the methods disclosed herein. The image can also be received from an application such as those which are available for handheld cellular devices and processed on the cellphone or other handheld computing device such as an iPad or Tablet-PC. The image can be received directly from a memory or storage device of the imaging device used to capture that image or video. The thermal image of the contra-lateral breast is analyzed to determine whether a hot spot exists in that breast.

Figure 4:
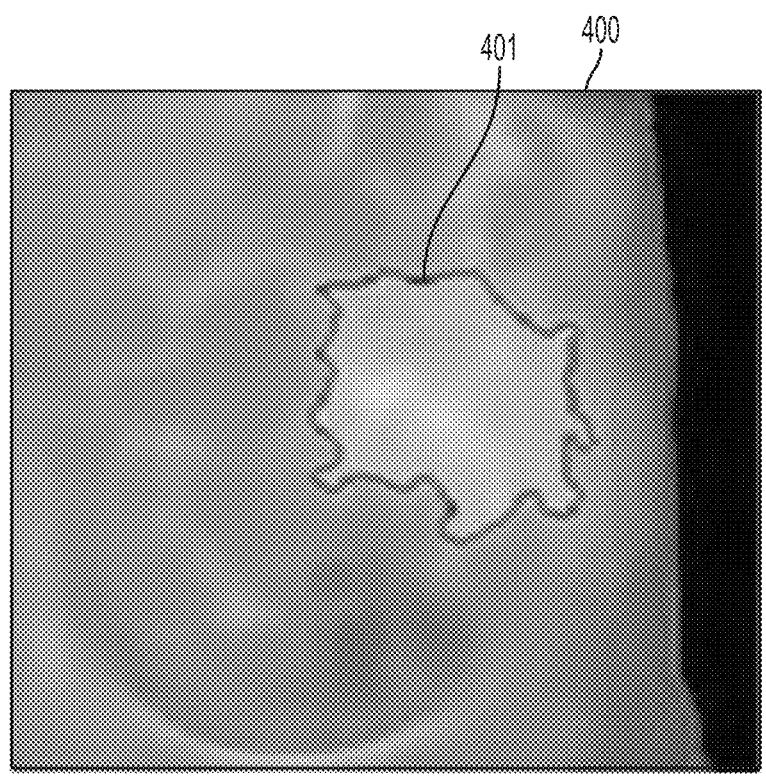
FIG. 4 shows a thermal image 400 of a right breast containing hot spot 401.

A "hot spot" refers to a patch of pixels with an elevated temperature relative to a temperature of pixels in surrounding tissue. FIG. 4 shows a thermal image 400 of a contra-lateral breast wherein a hot spot 401 is identified. A hot spot may be manually or automatically identified in the thermal image. A hot spot can be identified in a thermal image using, for example, temperatures of the isotherms of the thermal image or by a user making the selection. A temperature of a given patch of pixels can be based on a mean temperature of pixels in the patch, a median temperature of pixels in the patch, a highest temperature of pixels in the patch, and a normalized histogram of temperature values of pixels within the patch. Hot spots in the thermographic image are analyzed to determine hormone receptor status.

Figure 5:
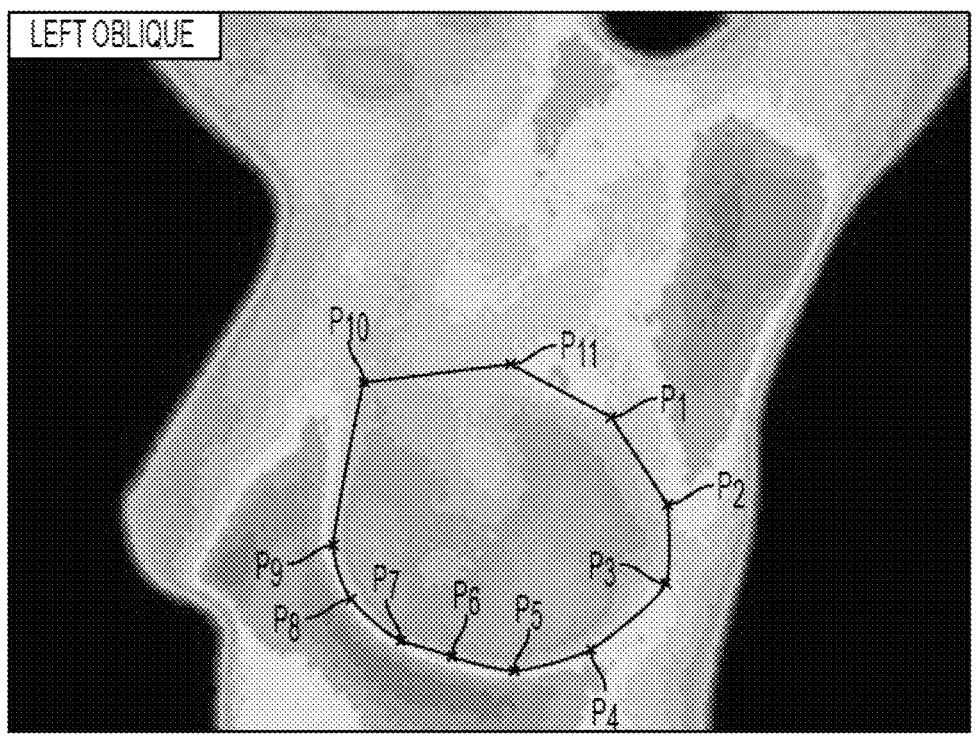
FIG. 5 shows a polygon defining a boundary of a breast in a thermal image.

A "boundary of the breast" means an area in the thermographic image that encompasses breast tissue. FIG. 5 shows a polygon defining a boundary of a breast in a thermal image. A boundary of the breast can be automatically identified and segmented in a thermographic image of the breast using, for example, a method as disclosed in U.S. patent application Ser. No. 15/055,140, entitled: "Automatic Segmentation Of Breast Tissue In A Thermographic Image", by Arun Koushik Parthasarathy et al., which teaches one embodiment of segmentation method for use in a breast cancer screening software tool wherein a thermographic image of a breast of a patient is analyzed to identify N points around the breast based on a contour of an outline of the patient's body and the isotherms of the patient's axilla and infra-mammary fold. The points are connected to form a N≥5 sided polygon which defines a boundary contour of the breast in the image. Each of the points is a vertex of the polygon. A user is enabled to selectively manipulate a shape of the polygon as desired or as is otherwise needed by moving or adjusting the vertices. A boundary of the breast can be manually identified in a thermographic image by a user using, for instance, a mouse or pen-pointer to draw boundary lines around the breast in the image displayed on display screen such as a touchscreen display.

A "hormone" is a chemical secreted into the blood stream by one or more specialized cells or groups of cells within the body. Hormones regulate bodily functions such as digestion, metabolism, growth, reproduction, mood, to name a few. Hormones are known to interact with other hormones in the blood stream. For example, the hormone estrogen interacts with the hormone progesterone to mediate lobuloalveolar maturation of the breasts upon pregnancy to allow for the onset of breast milk production. Hormones interacting with specialized cellular structures called "receptors" act like a lock & key. The cell's receptor (lock) receives the hormone (key). The key activates the lock which, in turn, mediates one or more cellular functions.

A "Hormone Receptor (HR)" is intended to include an Estrogen Receptor (ER), Progesterone Receptor (PR), Human Epidermal Receptor 2 (HER2), Tumor Cell Growth Protein Marker Ki67, or a combination thereof. There is variability in the different ER/PR/HER2 sub-types with ER status having an increased level of importance. A tumor that is ER+ (positive) has a lower mortality than a tumor that is ER− (negative). PR status generally has a lesser importance than ER status. Patients with a tumor that is PR+ have a lower mortality than patients with a tumor that is PR−. Studies show that ER−/PR− tumors are more aggressive than ER+/PR+ tumors. A patient with a tumor with ER+/PR+/HER2− status has a lower mortality risk than does a patient with a tumor with ER−/PR−/HER2− status. The Ki-67 status is a useful indicator of tumor cell growth rate.

Feature Extraction

The thermal image of the patient's breast region in the thermographic image is divided into abnormal and normal regions based on their regional temperatures. Abnormal regions correspond the suspicious regions in the breast region and have the highest regional temperature in the Region of Interest (ROI). To segment an abnormal region in a thermographic image of a breast, the present method utilizes a segmentation algorithm. One embodiment for performing segmentation is disclosed in commonly owned and co-pending U.S. patent application Ser. No. 15/055,140 entitled: "Automatic Segmentation Of Breast Tissue In A Thermographic Image", by Arun Koushik Parthasarathy et al. (filed: Feb. 26, 2016). Segmented areas are combined from multiple features defined by Eq. (4) and (5) using a decision rule.

$$T_1 = Mode(ROI) + \rho^*(T_{max} - Mode(ROI)) \quad (1)$$

$$T_2 = T_{max} - \tau \quad (2)$$

where $T_{max}$ represents the overall maximum temperature in all views, Mode(ROI) represents the mode of the histogram using all views, and parameters $\rho$, $\tau$ and the decision fusion rule are selected based on the accuracy of classification and diversity of features. From these detected abnormal regions, we extract the following features.

A "probability mass function (PMF)", is a probability measure that gives us probabilities of the possible values for a random variable and defines a discrete probability distribution. Such functions are known to exist for either scalar or multivariate random variables whose domain is discrete. The PMF gives probabilities of the possible values for a random variable. For discrete random variables, the PMF is also called the probability distribution. Thus, when asked to find the probability distribution of a discrete random variable, we find its PMF. In accordance with the teachings hereof, a distance is determined between two probability mass functions.

A "distance measure" refers to a distance between two probability mass functions. In one embodiment, the distance measure comprises:

$$JSD(P \| Q) = \frac{1}{2}\sum_i \left(\log \frac{P(i)}{M(i)}\right)P(i) + \frac{1}{2}\sum_i \left(\log \frac{Q(i)}{M(i)}\right)Q(i) \quad (3)$$

where Q is the first probability mass function, P is the second probability mass function, the distance measure decreasing as P and Q converge and increasing as P and Q diverge, and the probability measure M comprises:

$$M(i) = \frac{1}{2}(P(i) + Q(i)) \quad (4)$$

The distance measure of Eq. (3) is provided or is otherwise communicated to a classifier system wherein the hot spot is classified as hormone receptor positive (HR+) or hormone receptor negative (HR−), based at least in part on the determined distance measure.

In another embodiment, a second thermographic image of a contra-lateral breast of a patient is received and analyzed to define a boundary of the contra-lateral breast. Another probability mass function $Q_2 = Q - \mu_1$ is determined, where $\mu_1$ is a mean temperature of pixels in the hot spot identified in the contra-lateral breast. Another probability mass function $P_2 = P - \mu_2$ is determined, where $\mu_2$ is a mean temperature of pixels outside the hot spot identified in the contra-lateral breast but within the boundary of the contra-lateral breast. Thereafter, a second distance measure $DM(P_2\|Q_2)$ is determined and provided to the classifier system wherein the hot spot in the image is classified as one of: hormone receptor positive (HR+), and hormone receptive negative (HR−) based, at least in part, on the second distance measure.

"Relative Hotness" is a distance measure which, in one embodiment, is given by:

$$RH = \frac{1}{|A|} \sum_{x \in A} \sum_{y \in A} \|T(x, y) - \mu\|^2 \quad (5)$$

where $T(x,y)$ represents a pixel temperature value of the malignant side abnormal region at location $(x,y)$ in the image, $\mu$ represents a mean temperature of the contra-lateral side abnormal region pixels and $|A|$ represents the cardinality of all pixels in the tumorous tissue.

A "classifier system" or simply "classifier" comprises at least a processor and a memory with the processor retrieving machine readable program instructions from memory and executing those instructions causing the processor to classify tissue in a thermal image of the breast as being HR+ or HR−. Classifiers can take any of a variety of forms including a Support Vector Machine (SVM), a neural network, a Bayesian network, a Logistic Regression, Naïve Bayes, Randomized Forests, Decision Trees and Boosted Decision Trees, K-nearest neighbor, a Restricted Boltzmann Machine (RBM), as are understood in the machine learning arts, including a hybrid system comprising any combination thereof. For an in-depth discussion, the reader is directed to any of a wide variety of texts, including: "*Foundations of Machine Learning*", MIT Press (2012), ISBN-13: 978-0262018258, and "*Design and Analysis of Learning Classifier Systems: A Probabilistic Approach*", Springer (2008), ISBN-13: 978-3540798651. The classifier is training using a training set which, in various embodiments, comprises patient medical records and historical data. Based on the training set, the classifier sets a threshold value. Once trained, the classifier then utilizes the threshold for classification. The threshold can be user adjusted or user manipulated as needed to minimize false positives and/or false negatives. As new data sets or additional parameters are added to the training set used to train the classifier, the threshold or decision boundary used by the classifier will likely change accordingly. The classifier system is trained to classify a hot spot using a distance measure.

It should be appreciated that the steps of "receiving", "analyzing", "communicating", "performing", "determining", "selecting", "providing", "training" and the like, as used herein, include the application of any of a variety of techniques as well as mathematical operations according to any specific context or for any specific purpose. Such steps may be facilitated or otherwise effectuated by a microprocessor executing machine readable program instructions such that the intended functionality is effectively performed.

Flow Diagram of One Embodiment

Figure 6:
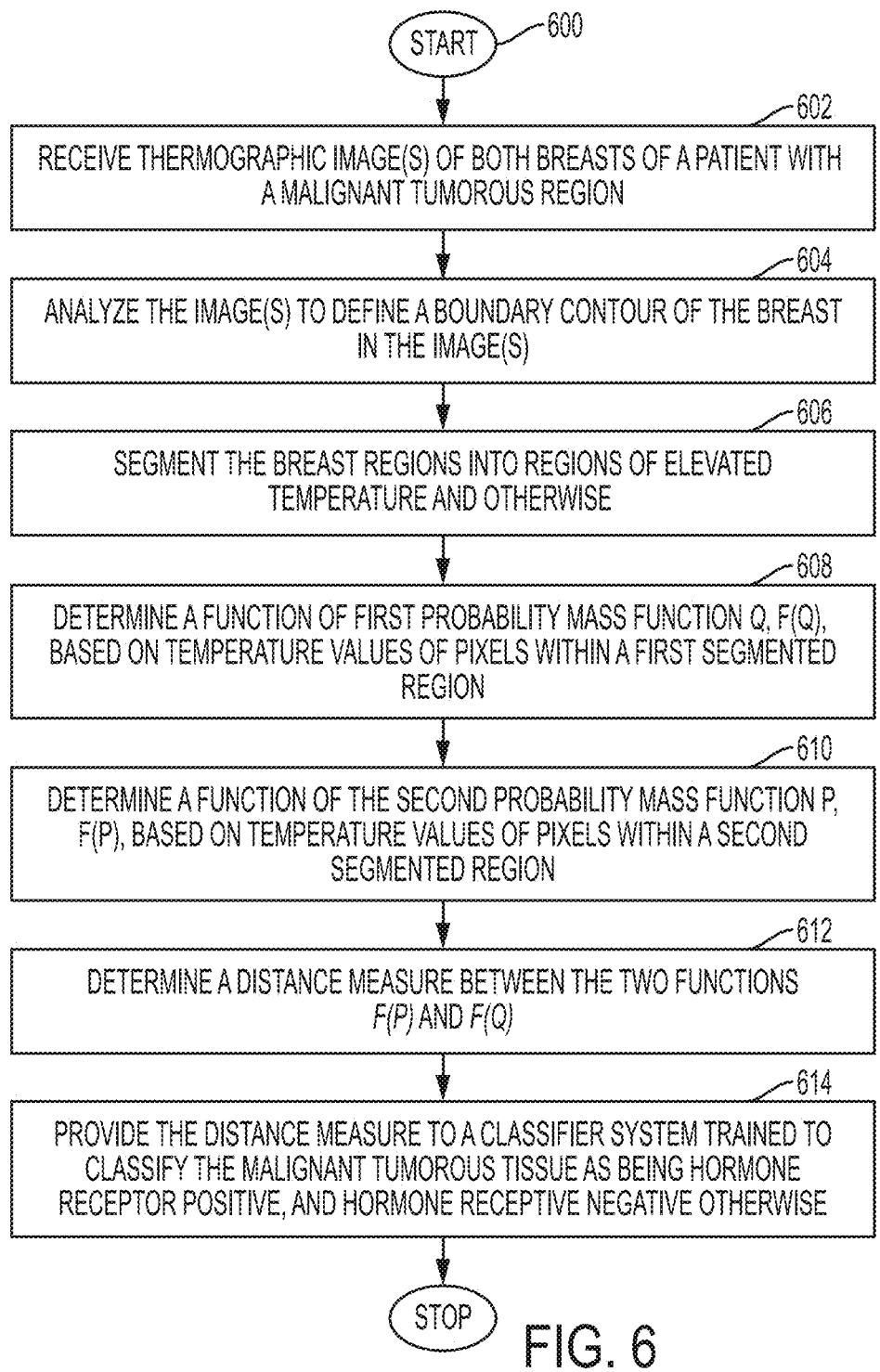
FIG. 6 is a flow diagram which illustrates one embodiment of the present method for classifying the hormone receptor status of malignant tumorous tissue identified in a thermographic image of a breast.

Reference is now being made to the flow diagram of FIG. 6 which illustrates one embodiment of the present method for classifying the hormone receptor status of malignant tumorous tissue identified in a thermographic image of a breast. Flow processing begins at step 600 and immediately proceeds to step 602.

At step 602, receive thermographic image(s) of both breasts of a patient with a malignant tumorous region.

At step 604, analyze the image(s) to define a boundary contour of the breast in the image(s).

At step 606, segment the breast regions into regions of elevated temperature and otherwise.

At step 608, determine a function of first probability mass function Q, $f(Q)$, based on temperature values of pixels within a first segmented region.

At step 610, determine a function of the second probability mass function P, $f(P)$, based on temperature values of pixels within a second segmented region.

At step 612, determine a distance measure between the two functions $f(P)$ and $f(Q)$.

At step 614, provide the distance measure to a classifier system trained to classify the malignant tumorous tissue as being hormone receptor positive, and hormone receptive negative otherwise. In this embodiment further processing stops. It should be appreciated that other steps may be undertaken by a medical professional in response to the classification as the medical professional deems is necessary or is otherwise desired given their patient's health, circumstance, condition, or medical history. Since such additional steps are necessarily patient dependent, a discussion as to particular steps that should or should not be taken is omitted herein as being beyond the scope of the appended claims. In another embodiment, in response to the classification, an alert is generated. The alert may take the form of a message displayed on a display device or a sound activated at, for example, a nurse's station. The alert may take the form of a colored or blinking light which provides a visible indication that an alert condition exists. The alert can be a text, email, audio, phone call, and/or a video message. The alert may include images of the hot spots, and/or aspects of processing such as results of the measure of symmetry, interim values, and the like. The alert may be communicated to one or more remote devices over a wired or wireless network. The alert may be sent directly to a handheld wireless cellular device of a medical professional.

Flow Diagram of Second Embodiment

Figure 7:
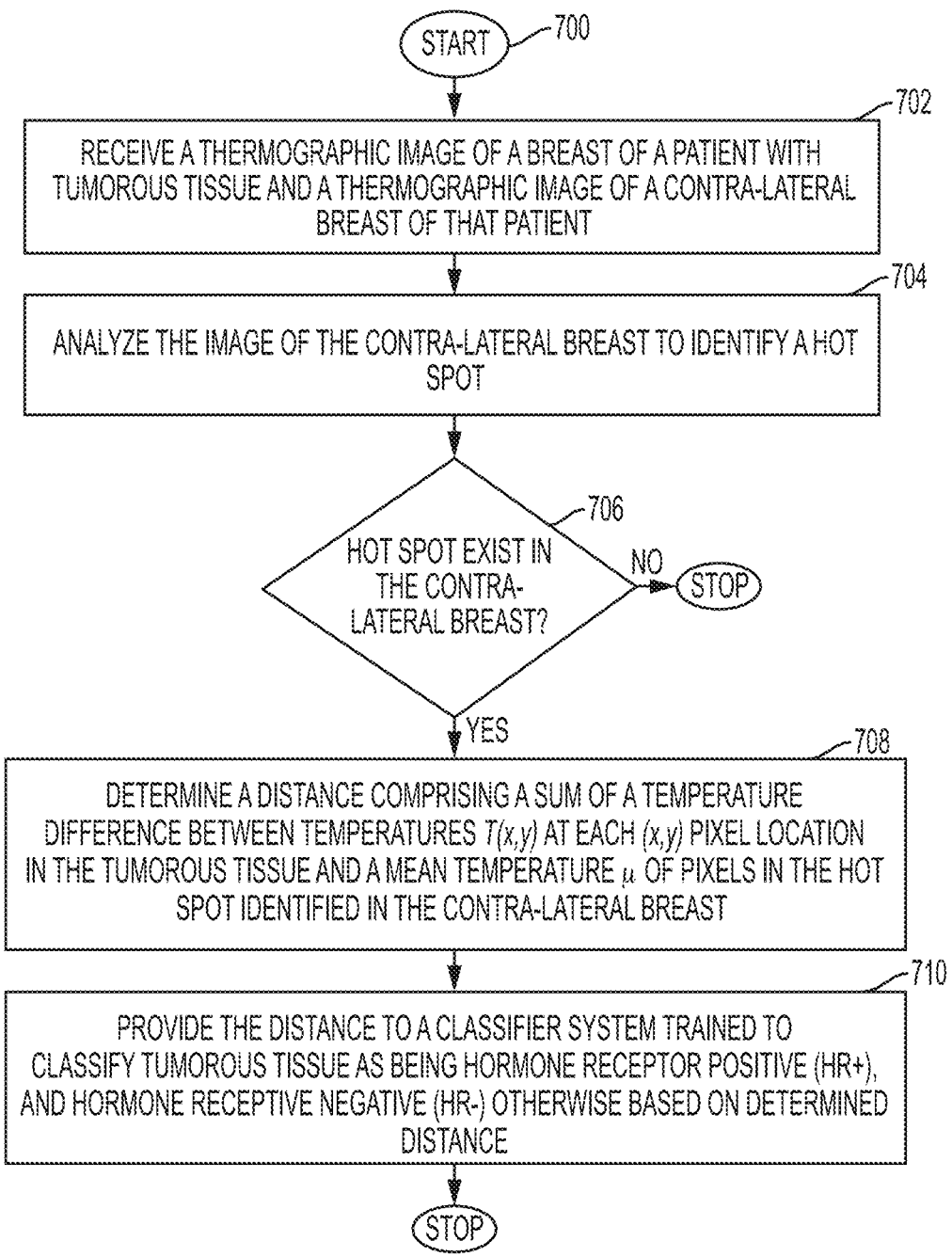
FIG. 7 is a flow diagram which illustrates one embodiment of the present method for classifying the hormone receptor status of tumorous tissue identified in a thermographic image of a breast based on a distance measure comprising a measure of relative hotness.

Reference is now being made to the flow diagram of FIG. 7 which illustrates one embodiment of the present method for classifying the hormone receptor status of tumorous tissue identified in a thermographic image of a breast based on a distance measure comprising a measure of relative hotness. Flow processing begins at step 700 and immediately proceeds to step 702.

At step 702, receive a thermographic image of a breast of a patient with tumorous tissue and a thermographic image of a contra-lateral breast of that patient. An example thermographic image of a breast with tumorous tissue is shown in FIG. 3. The thermographic image can be a single image of both breasts or separate images of each of the left and right breast.

At step 704, analyze the image of the contra-lateral breast to identify a hot spot. A hot spot is a patch of pixels with an elevated temperature with respect to a temperature of pixels in surrounding tissue. An example hot spot of the contra-lateral breast is shown in FIG. 4.

At step 706, a determination is made whether a hot spot exists in the image of the contra-lateral breast. If not, in this embodiment, further processing stops.

At step 708, extract a distance measure comprising a sum of a temperature difference between temperatures T(x,y) at each (x,y) pixel location in the tumorous tissue and a mean temperature $\mu$ of pixels in the hot spot identified in the contra-lateral breast. In this embodiment, the distance measure comprises a measure of relative hotness as discussed with respect to Eq. (5).

At step 710, provide the distance measure to a classifier system trained to classify tumorous tissue as being hormone receptor positive (HR+), and hormone receptive negative (HR−) otherwise. In this embodiment further processing stops. It should be appreciated that other steps may be undertaken by a medical professional in response to the classification as the medical professional deems is necessary or is otherwise desired given their patient's health, circumstance, condition, or medical history. Since such additional steps are necessarily patient dependent, a discussion as to particular steps that should or should not be taken is omitted herein as being beyond the scope of the appended claims. In another embodiment, in response to the classification, an alert is generated. The alert may take the form of a message displayed on a display device or a sound activated at, for example, a nurse's station. The alert may take the form of a colored or blinking light which provides a visible indication that an alert condition exists. The alert can be a text, email, audio, phone call, and/or a video message. The alert may include images of the hot spots, and/or aspects of processing such as results of the measure of symmetry, interim values, and the like. The alert may be communicated to one or more remote devices over a wired or wireless network. The alert may be sent directly to a handheld wireless cellular device of a medical professional.

It should be understood that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims. All or portions of the flow diagrams may be implemented partially or fully in hardware in conjunction with machine readable/executable program instructions.

Block Diagram of Image Processing System

Figure 8:
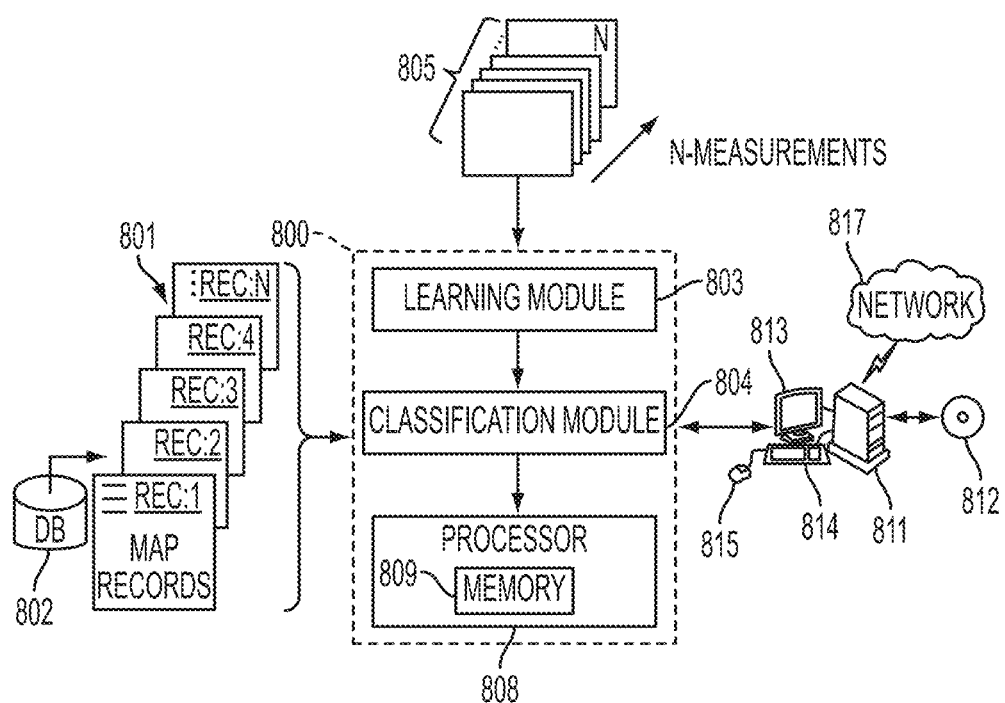
FIG. 8 shows a functional block diagram of one example image processing system for processing thermographic images for breast cancer screening in accordance with the embodiment described with respect to the flow diagrams of FIG. 6.

Reference is now being made to FIG. 8 which shows a functional block diagram of one example image processing system for processing thermographic images for breast cancer screening in accordance with the embodiment described with respect to the flow diagram of the embodiment of FIG. 6.

A training set (collectively at 801) comprising records containing thermal images, hot spots, various receptor status', medical records of patients, and the like, are retrieved from a database 802 comprising a storage device. Although the database is shown as an external device, the database may be internal to the workstation 811 mounted, for example, on a hard disk. The training set is provided to a classifier system 800. In the embodiment shown, the classifier system comprises a Learning Module 803 which processes the training set 801 such that the classifier system can determine an appropriate threshold such that the hormone receptor status of a given hot spot in a thermal image of the breast can be classified. Learning Module 803 may further be configured to prune the training set, as needed or as desired, such that the classifier is trained with data which meets a pre-determined criteria of acceptability, at least for accuracy such that false positives and false negatives are minimized. Once training has completed, Learning Module 803 signals the Processor 808 to receive a total of n thermal images of the breast of a patient undergoing breast cancer screening in accordance with the methods disclosed herein (collectively at 805) where n≥1. It should be appreciated that the received thermal images 805 have been acquired by the imaging device 101 and represent thermographic images such as those in FIGS. 2, 3 and 4. The thermographic images can be communicated directly to the classifier system 800 via wired or wireless pathways (not shown). Some or all of the functionality of the classifier system 800 may be integrated in the imaging device 101.

Processor 808 retrieves machine readable program instructions from Memory 809 to analyze the thermographic images to define a boundary contour of the breast in the image(s); segment the breast regions into regions of elevated temperature and otherwise; determine a function of first probability mass function Q, $f(Q)$, based on temperature values of pixels within a first segmented region; determine a function of the second probability mass function P, $f(P)$, based on temperature values of pixels within a second segmented region; and determine a distance between the two functions $f(P)$ and $f(Q)$. The processor communicates the determined distance to the Classification Module 804 which proceeds to classify the hormone receptor status of the hot spot in the image based on the determined distance. In another embodiment, the processor is configured to extract a distance measure comprising a distance measure and to communicate the distance measure to the classifier trained which proceeds to classify tumorous tissue as being hormone receptor positive (HR+), and hormone receptive negative (HR−) otherwise, based on the determined distance measure.

System 800 is shown having been placed in communication with a workstation 811. A computer case of the workstation houses various components such as a motherboard with a processor and memory, a network card, a video card, a hard drive capable of reading/writing to machine readable media 812 such as a floppy disk, optical disk, CD-ROM, DVD, magnetic tape, and the like, and other software and hardware needed to perform the functionality of a computer workstation. The workstation further includes a display device 813, such as a CRT, LCD, or touch screen device, for displaying information, images, classifications, video, measurement data, computed measures of symmetry, medical information, results, interim values, and the like. A user can view any of that information and make a selection from menu options displayed thereon. Keyboard 814 and mouse 815 effectuate a user input. It should be appreciated that the workstation 811 has an operating system and other specialized software configured to display alphanumeric values, menus, scroll bars, dials, slideable bars, pull-down options, selectable buttons, and the like, for entering, selecting, modifying, and accepting information needed for processing in accordance with the teachings hereof.

The workstation is further enabled to display thermal images, hot spots, and classifications as they are derived. The workstation can further display interim values, boundary conditions, and the like, in real-time as the Classification Module 804 performs its functionality. A user or technician may use the user interface of the workstation 811 to set parameters, view/adjust/delete values in the training set, and adjust various aspects of the classifier system as needed or as desired, depending on the implementation. Any of these selections or input may be stored/retrieved to storage device 812. Default settings can be retrieved from the storage device. A user of the workstation is also able to view or manipulate any of the data in the records comprising the training set 801. The training set may be stored to a storage device internal to the workstation 811. Although shown as a desktop computer, the workstation 811 can be a laptop, mainframe, or a special purpose computer such as an ASIC, circuit, or the like. The embodiment of the workstation of FIG. 8 is illustrative and may include other functionality known in the arts.

Any of the components of the workstation may be placed in communication with the classifier system 800 or any devices in communication therewith. Any of the modules of the classifier system can be placed in communication with storage device 802 and/or computer readable media 812 and may store/retrieve there from data, variables, records, parameters, functions, and/or machine readable/executable program instructions, as needed to perform their intended functions. Each of the modules of the classifier system 800 may be placed in communication with one or more remote devices over network 817. It should be appreciated that some or all of the functionality performed by any of the modules or processing units of the system 800 can be performed, in whole or in part, by the workstation. The embodiment shown is illustrative and should not be viewed as limiting the scope of the appended claims strictly to that configuration. Various modules may designate one or more components which may, in turn, comprise software and/or hardware designed to perform the intended function.

Performance Results

An anonymized dataset of 56 subjects with biopsy confirmed breast cancer with ages varying from 27 to 76 years was obtained through a collaboration with an area hospital. A FLIR E60 camera with a spatial resolution of 320×240 pixels was used to capture thermographic images of the initial 20 subjects. A high-resolution FLIR T650Sc camera with an image resolution of 640×480 pixels was used to capture thermographic images of the remaining subjects. The acquisition protocol involved asking the subject to rotate from right lateral to left lateral views. The data for each subject included the mammography, sonomammography, biopsy reports, and the ER/PR status values of the tumors. The HER2 and Ki67 status, where available, was also present for most patients. From this data, there were 32 subjects with HR+ malignant tumors and rest of them have HR− tumors.

From the obtained videos, we manually selected five frames that corresponds to frontal, right & left oblique views and right & lateral views. Manual cropping was done on these five views to select the ROI. Consideration of multiple views helps in better tumor detection since it might not be seen in a fixed view. From these multiple views, the view corresponding to maximum abnormal region area with respect to the ROI area was considered as the best view. In addition to the temperature change, the areas of the abnormal regions on both sides are also considered as features. The ratio of areas of abnormal regions on the contralateral side to the malignant side can be used. This value tends to zero for HR− tumors and is higher for HR+ tumors.

Textural features can also be used here to extract the features from the entire ROI. Instead of using the original temperature map of the ROI, a modified temperature map is used. The thermal map formed by subtracting the malignant side ROI with the contra-lateral side mean temperature is used to determine the textural features. The Run Length Matrix (RLM) is computed from the thermal map, after quantizing the temperature into I bins. Gray level non-uniformity and Energy features from the RLM are computed, as mentioned in "*Thermography based breast cancer detection using texture features and support vector machine*", Acharya, U. R., Ng, E., Tan, J. H., Sree, S. V., Journal of medical systems 36(3), 1503-1510 (2012). The non-uniformity feature would be higher for HR− tumors as their tumors have more focal temperatures.

The best view along with its contra-lateral side view was used to calculate the features from the abnormal regions and the entire ROI. The training set and testing set comprised a randomly chosen subset of 26 and 30 subjects, respectively, with an internal division of 14 HR+ & 12 HR− and 18 HR+ & 12 HR− tumors, respectively. The abnormal region was located using $\rho=0.2$, $\tau=3°$ C. with the AND decision rule, to optimize for the accuracy in classification. The bin width of the PMFs used was 0.5° C. The step size of the temperature bins in the RLM computation was 0.25° C.

A two-class Random Forest ensemble classifier was trained using the features obtained. The Random Forest (RF) randomly chooses a training sub-set & a feature sub-set for training a decision tree, and combines the decisions from multiple such trees to get more accuracy in classification. The mode of all trees is taken as the final classification decision. RFs with 100 decision trees are used and the maximum accuracy found in 20 iterations is noted. Table of FIG. 9 shows accuracies obtained using individual features using the methods disclosed herein. We tested with different textural features obtained from both RLM and Gray Level Co-occurrence Matrix, but found that gray-level non-uniformity from the RLM was having better accuracy than others. Using an optimal combined set of region based features and textural features, we obtained an accuracy of 82% and 79% in classification of HR+ and HR− tumors respectively. In sum, the methods disclosed herein to classify tumors as being one of: HR+ or HR− using thermography performed with an accuracy of around 80% and presents an advantage to thermography over other imaging modalities. The classification is useful in estimating prognosis and treatment planning for breast cancer patients.

Various Embodiments

The teachings hereof can be implemented in hardware or software using any known or later developed systems, structures, devices, and/or software by those skilled in the applicable art without undue experimentation from the functional description provided herein with a general knowledge of the relevant arts. One or more aspects of the methods described herein are intended to be incorporated in an article of manufacture which may be shipped, sold, leased, or otherwise provided separately either alone or as part of a product suite or a service. It will be appreciated that the above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any publications referenced herein are hereby incorporated by reference in their entirety.

What is claimed is:

1. A method for classifying the hormone receptor status of malignant tumorous tissue identified in a thermographic image of a breast, the method comprising:
receiving thermographic image(s) of both breasts of a patient with a malignant tumorous region;
segmenting the breast regions into regions of elevated temperature and otherwise; and
analyzing temperature distribution of the thermographic image of the whole breast and the elevated temperature regions to classify the malignant tumorous tissue as being hormone receptor positive, and hormone receptive negative otherwise, wherein said analyzing the elevated temperature regions comprises comparison of the temperature distribution of the segmented regions, wherein said analyzing for the entire breast region comprises extracting a gray-level co-occurrence matrix (GLCM) and other textural features and using the co-occurrence features of the two breasts for classifying malignant tumorous tissue,
where a first segmented region is the elevated temperature region corresponding to the malignant tumorous tissue region; a second segmented region is the non-elevated temperature region in the same breast, wherein a distance measure representing a similarity between the first segmented region and the second segmented region is determined, and wherein the distance measure is provided to a classifier system to classify the hormone receptor class as either positive or negative.

2. The method of claim 1,
wherein the first segmented region is represented by probability mass function P based on temperature values of pixels within the first segmented region, wherein the second segmented region is represented by probability mass function Q based on temperature values of pixels within the second segmented region, wherein a distance measure between the two functions P and Q is determined, and wherein the distance measure is provided to the classifier system to classify the hormone receptor class as either positive or negative.

3. The method of claim 2, wherein the first segmented region is the elevated temperature region corresponding to the malignant tumorous tissue region; the second segmented region is the non-elevated temperature region in the same breast; the function of the first probability mass function is the normalization after subtracting the mean temperature of a third elevated temperature region in the contralateral breast to the malignant tumorous breast; the function of the second probability mass function is the normalization after subtracting the mean temperature of a fourth non-elevated temperature region in the contralateral breast to the malignant tumorous breast.

4. The method of claim 2, wherein the first segmented region is the elevated temperature region corresponding to the malignant tumorous tissue region; the second segmented region is the elevated temperature region in the contralateral breast; $f(Q)=\Sigma_i i Q(i)$; $f(P)=\Sigma_i i P(i)=\mu_p$; the distance function is the mean squared distance between $f(Q)$ and $f(P)$ given by $\Sigma_i \|i-\mu_p\|^2 Q(i)$, where the $f(Q)$ is a function of first probability mass function Q, the (P) is a function of second probability mass function P, the i is a iterator variable, the Q(i) is a iterator variable of the first probability mass function Q, the P(i) is a iterator variable of the second probability mass function Q, and the $\mu_p$ is a mean of P.

5. The method of claim 2, wherein the first segmented region is the non-elevated temperature region corresponding to the same breast having the malignant tumorous tissue; the second segmented region is the elevated temperature region in the contralateral breast; $f(Q)=\Sigma_i i Q(i)$; $f(P)=\Sigma_i i P(i)=\mu_p$; the distance function is the mean squared distance between $f(Q)$ and $f(P)$ given by $\Sigma_i \|i-\mu_p\|^2 Q(i)$, where the $f(Q)$ is a function of first probability mass function Q, the $f(P)$ is a function of second probability mass function P, the i is a iterator variable, the Q(i) is a iterator variable of the first probability mass function Q, the P(i) is a iterator variable of the second probability mass function Q, and the $\mu_p$ is a mean of P.

6. The method of claim 2, where Q is obtained by normalizing corresponding histograms of pixels comprising the segmented region.

7. The method of claim 2, wherein the distance function can be the Jensen Shannon distance, the Kullback Liebler distance, mutual information, or any standard defined distance function between two probability mass functions.

8. The method of claim 1, further comprising:
receiving a thermographic image of a contra-lateral breast of the patient;
analyzing the thermographic image to identify a hot spot in the contra-lateral breast, the hot spot comprising a patch of pixels with an elevated temperature with respect to surrounding tissue;
determining a second distance measure between P−$\mu_1$ and Q−$\mu_2$, where $\mu_1$ is a mean temperature of the hot spot identified in the contra-lateral breast, and $\mu_2$ is the mean temperature of the surrounding tissue in the contra-lateral breast, where Q is the PMF of the hotspot related to the malignant tumorous tissue, and P is the PMF of the normal region in the breast having the malignant tumor; and
providing the second distance measure the classifier system.

9. The method of claim 1, wherein the classifier system comprises any of: Support Vector Machine, a neural network, a Bayesian network, a Logistic regression, Naïve Bayes, Randomized Forests, Decision Trees and Boosted Decision Trees, K-nearest neighbor, a Restricted Boltzmann Machine, and a hybrid system comprising any combination hereof.

10. The method of claim 1, wherein, in response to more than one hot spot being identified in either the left or right breast, further comprising selecting one of the hot spots for comparison purposes.

11. The method of claim 1, further comprising updating a training set use to train the classifier system with the classified hot spot.

12. The method of claim 1, further comprising communicating the classification to any of: a storage device, a display device, and a remote device over a network.

13. A system for classifying the hormone receptor status of malignant tumorous tissue identified in a thermographic image of a breast, the system comprising:
a storage device containing a classifier system trained to classify a hot spot as one of: hormone receptor positive (HR+), and hormone receptive negative (HR−); and
a processor in communication with the storage device, the processor retrieving executing machine readable program instructions which, when executed by the processor, enable the processor to:
receive thermographic image(s) of both breasts of a patient with a malignant tumorous region;
analyze the image(s) to define a boundary contour of the breast in the image(s);
segment the breast regions into regions of elevated temperature and otherwise; and
analyze temperature distribution of the thermographic image of the whole breast and the elevated temperature regions to classify the malignant tumorous tissue as being hormone receptor positive, and hormone receptive negative otherwise, wherein said analyzing the elevated temperature regions comprises comparison of the temperature distribution of the segmented regions, wherein said analyzing for the entire breast region comprises extracting a gray-level co-occurrence matrix (GLCM) and other textural features and using the co-occurrence features of the two breasts for classifying malignant tumorous tissue,
where a first segmented region is the elevated temperature region corresponding to the malignant tumorous tissue region; a second segmented region is the non-elevated temperature region in the same breast, wherein a distance measure representing a similarity between the first segmented region and the second segmented region is determined, and wherein the distance measure is provided to a classifier system to classify the hormone receptor class as either positive or negative.

14. The system of claim 13, wherein the first segmented region is represented by probability mass function P based on temperature values of pixels within the first segmented region, wherein the second segmented region is represented by probability mass function Q based on temperature values of pixels within the second segmented region, wherein the processor is configured to determine a distance measure between the two functions P and Q, and wherein the distance measure is provided to the classifier system to classify the hormone receptor class as either positive or negative.

15. The system of claim 14, wherein the first segmented region is the elevated temperature region corresponding to the malignant tumorous tissue region; the second segmented region is the non-elevated temperature region in the same breast; the function of the first probability mass function is the normalization after subtracting the mean temperature of a third elevated temperature region in the contralateral breast to the malignant tumorous breast; the function of the second probability mass function is the normalization after subtracting the mean temperature of a fourth non-elevated temperature region in the contralateral breast to the malignant tumorous breast.

16. The system of claim 14, where Q is obtained by normalizing corresponding histograms of pixels comprising the segmented region.

17. The system of claim 14, wherein the distance function can be the Jensen Shannon distance, the Kullback Liebler distance, mutual information, or any standard defined distance function between two probability mass functions.

18. The system of claim 13, wherein the first segmented region is the elevated temperature region corresponding to the malignant tumorous tissue region; the second segmented region is the elevated temperature region in the contralateral breast; $f(Q)=\Sigma_i iQ(i)$; $f(P)=\Sigma_i iP(i)=\mu_p$; the distance function is the mean squared distance between $f(Q)$ and $f(P)$ given by $\Sigma_i \|i-\mu_p\|^2 Q(i)$, where the $f(Q)$ is a function of first probability mass function Q the $f(P)$ is a function of second probability mass function P, the i is a iterator variable, the Q(i) is a iterator variable of the first probability mass function Q, the P(i) is a iterator variable of the second probability mass function Q and then is a mean of P.

19. The system of claim 13, wherein the first segmented region is the non-elevated temperature region corresponding to the same breast having the malignant tumorous tissue; the second segmented region is the elevated temperature region in the contralateral breast; $f(Q)=\Sigma_i iQ(i)$; $f(P)=\Sigma_i iP(i)=\mu_p$; the distance function is the mean squared distance between $f(Q)$ and $f(P)$ given by $\Sigma_i \|i-\mu_p\|^2 Q(i)$, where the AO is a function of first probability mass function Q, the $f(P)$ is a function of second probability mass function P, the i is a iterator variable, the Q(i) is a iterator variable of the first probability mass function Q, the P(i) is a iterator variable of the second probability mass function Q, and the $\mu_p$ is a mean of P.

20. The system of claim 13, wherein the processor is further configured to:
   receive a thermographic image of a contra-lateral breast of the patient;
   analyze the thermographic image to identify a hot spot in the contra-lateral breast, the hot spot comprising a patch of pixels with an elevated temperature with respect to surrounding tissue;
   determine a second distance measure between P–$\mu_1$ and Q–$\mu_2$, where $\mu_1$ is a mean temperature of the hot spot identified in the contra-lateral breast, and $\mu_2$ is the mean temperature of the surrounding tissue in the contra-lateral breast, where Q is the PMF of the hotspot related to the malignant tumorous tissue, and P is the PMF of the normal region in the breast having the malignant tumor; and
   provide the second distance measure to the classifier system.

21. The system of claim 13, wherein the classifier system comprises any of: Support Vector Machine, a neural network, a Bayesian network, a Logistic regression, Naïve Bayes, Randomized Forests, Decision Trees and Boosted Decision Trees, K-nearest neighbor, a Restricted Boltzmann Machine, and a hybrid system comprising any combination hereof.

22. The system of claim 13, wherein, in response to more than one hot spot being identified in either the left or right breast, further comprising selecting one of the hot spots for comparison purposes.

23. The system of claim 13, wherein the processor is further configured to update a training set use to train the classifier system with the classified hot spot.

24. The system of claim 13, wherein the processor is further configured to communicate the classification to any of: a display device, and a remote device over a network.

25. A method for classifying the hormone receptor status of malignant tumorous tissue identified in a thermographic image of a breast, the method comprising:
   receiving thermographic image(s) of both breasts of a patient with a malignant tumorous region;
   analyzing the image(s) to define a boundary contour of the breast in the image(s);
   generating a temperature map by subtracting the pixel temperatures of the malignant breast with the mean temperature of the contra-lateral breast;
   computing a Run-Length-Matrix from the above temperature map, after quantizing the temperatures into L bins;
   computing textural non-uniformity features from the Run Length Matrix; and
   classifying the malignant tumorous tissue as hormone receptor negative if the non-uniformity feature is higher or hormone receptor positive otherwise, using a classifier system.

26. The method of claim 25, wherein additional energy features and other textural features from the temperature map are used as additional inputs to the classifier system to determine whether the malignant tumorous tissue is hormone receptor positive or negative.

27. A method for classifying the hormone receptor status of malignant tumorous tissue identified in a thermographic image of a breast, the method comprising:
   receiving thermographic image(s) of both breasts of a patient with a malignant tumorous region;
   analyzing the image(s) to define a boundary contour of the breast in the image(s);
   segmenting the breast regions into regions of elevated temperature and otherwise;
   determining the ratio between the area of elevated temperature region(s) in the malignant tumorous breast and the area of the elevated temperature region(s) in the contralateral breast, or vice-versa by analyzing the elevated temperature regions, wherein said analysis of the elevated temperature regions comprises the step of (i) comparison of temperature distribution of the segmented regions and (ii) extracting a gray-level co-occurrence matrix (GLCM) and other textural features and using the co-occurrence features of the two breasts for classifying malignant tumorous tissue;
   providing the above area ratio and co-occurrence of features to the classifier system: and
   classifying the malignant tumorous region as hormone receptor positive if the ratio is higher or hormone receptor negative if the ratio is zero, using a classifier system.

* * * * *